United States Patent

Regnier et al.

Patent Number: 4,548,820
Date of Patent: Oct. 22, 1985

[54] XANTHINE COMPOUNDS

[75] Inventors: Gilbert Regnier, Chatenay Malabry; Claude Guillonneau, Clamart; Jacques Duhault, Croissy sur Seine; Michelle Boulanger, Marly le Roi, all of France

[73] Assignee: Adir, Neuilly-sur-Seine, France

[21] Appl. No.: 516,946

[22] Filed: Jul. 25, 1983

[30] Foreign Application Priority Data

Jul. 28, 1982 [FR] France .................. 82 13155

[51] Int. Cl.[4] ............ C07D 473/08; A61K 31/52
[52] U.S. Cl. ......................... 514/255; 544/267; 544/269; 514/265
[58] Field of Search .......... 544/277, 266, 267, 269; 424/253

[56] References Cited

U.S. PATENT DOCUMENTS 4,416,878  11/1983  Klosa ........................... 426/253
4,426,383  1/1984   Sugimoto et al. ............. 544/267
4,493,837  1/1985   Sugimoto et al. ............. 424/253

FOREIGN PATENT DOCUMENTS 0095188  8/1981  Japan.

Primary Examiner—Nicholas S. Rizzo
Attorney, Agent, or Firm—Gordon W. Hueschen

[57] ABSTRACT

New xanthine compounds of the formula:

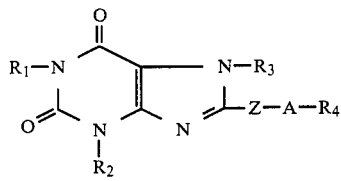

in which:

$R_1$ is hydrogen or alkyl from $C_1$ to $C_5$ inclusive;
$R_2$ is a hydrocarbon radical up to $C_6$ having optionally a double bond, phenyl or benzyl;
$R_3$ is hydrogen, alkyl, hydroxyalkyl or dihydroxyalkyl each from $C_1$ to $C_5$
$R_4$ represents:

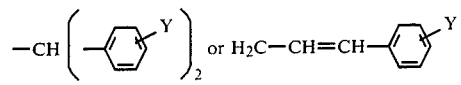

in which:
Y is hydrogen, halogen, alkyl or alkoxy from $C_1$ to $C_5$ or hydroxyl;
Z is methylene or a straight or branched hydrocarbon radical from $C_2$ to $C_5$ optionally substituted by hydroxyl; and
A is an amino group of the formula:

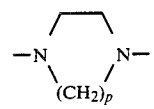

p being 2 or 3;

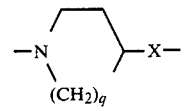

in which q is 1 or 2, and X is a single bond, oxygen or

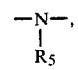

in which $R_5$ is hydrogen, alkyl or alkylene up to $C_5$, or

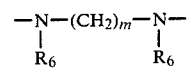

in which m is an integer from 2 to 6 and $R_6$ is alkyl from $C_1$ to $C_5$.

These new compounds and physiologically tolerable acid addition salts thereof may be used as medicines especially in the treatment of all diseases where it is necessary to inhibit the antigenic antibody reactions.

13 Claims, No Drawings

XANTHINE COMPOUNDS

The present invention provides xanthine compounds of the formula:

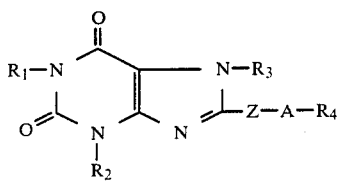

(I)

in which:

R₁ is selected from the group consisting of a hydrogen atom and alkyl radicals having from 1 to 5 carbon atoms inclusive in straight and branched chain;

R₂ is selected from the group consisting of straight chain and branched hydrocarbon radicals containing up to 6 carbon atoms inclusive, these hydrocarbon radicals including a double bond, phenyl and benzyl radicals;

R₃ is selected from the group consisting of a hydrogen atom, alkyl, hydroxyalkyl and dihydroxyalkyl radicals each having from 1 to 5 carbon atoms inclusive;

R₄ is selected from the group consisting of radicals of the formula:

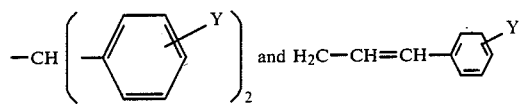

in which:

Y is a substituent selected from the group consisting of a hydrogen atom, halogen atoms, alkyl and alkoxy radicals each having from 1 to 5 carbon atoms inclusive, and a hydroxy radical;

Z is selected from the group consisting of a methylene radical, straight and branched hydrocarbon radicals having from 2 to 5 carbon atoms and these hydrocarbon radicals substituted by a hydroxy radical; and A is an amino residue selected from the group consisting of:

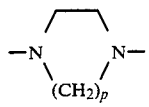

in which p is an integer selected from 2 and 3;

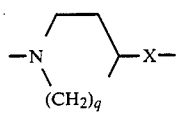

in which q is an integer selected from 1 and 2, and X is selected from the group consisting of a single bond, an oxygen atom and a

radical in which R₅ is selected from the group consisting of a hydrogen atom and a alkyl and alkylene radicals each having from 1 to 5 carbon atoms; and

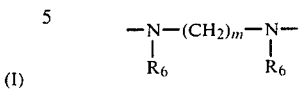

in which: m is an integer selected from 2 to 6 inclusive, and R₆ is selected from the group consisting of alkyl radicals having from 1 to 5 carbon atoms inclusive.

The present invention also provides the process for preparing the compounds of the formula (I) characterized in that:

a halo compound of the formula (II)

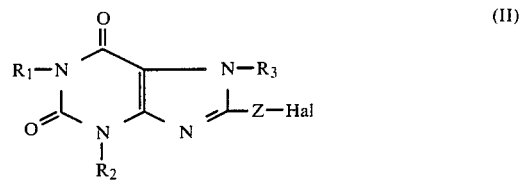

(II)

in which R₁, R₂, R₃ and Z have the meanings previously defined, and Hal is selected from the group consisting of chlorine and bromine atoms, is condensed with an amino compound of the formula III:

HA—R₄    (III)

in which A and R₄ have the meanings previously defined.

The condensation is preferably carried out in a solvent chosen from the alcohols containing up to 5 carbon atoms, such, for example, as methanol, ethanol, propanol or butanol. It is advantageous to operate at a temperature between 64° and 130° C., in the presence of an acceptor of the hydracid formed during the reaction. This acceptor may be chosen from the alkaline carbonates such as sodium and potassium carbonates, tertiary amines, such as triethylamine or an excess of the amino compound of the formula (III) used for the reaction.

The starting materials of the formula (II) have been prepared according to the following operational scheme:

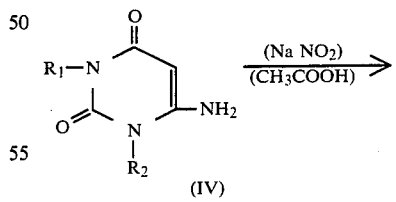

(IV)

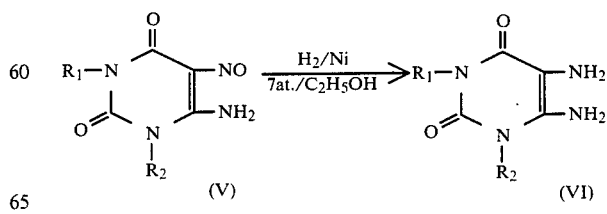

(V)    (VI)

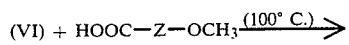

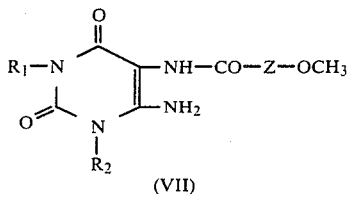

(VII)

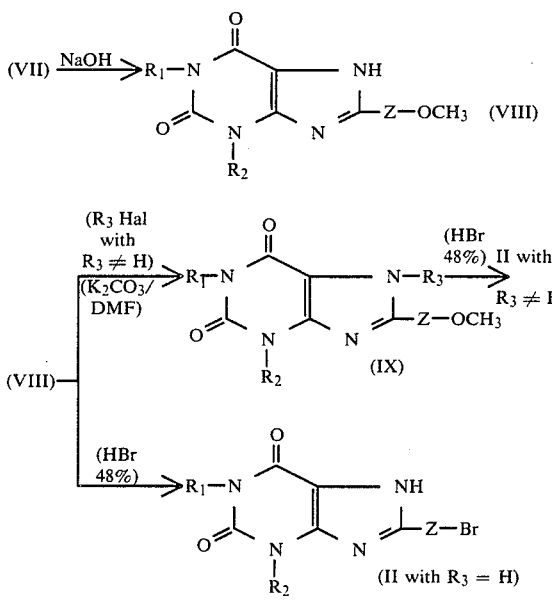

The starting materials of the general formula (III) are known products.

The present invention also provides a process for preparing compounds of the formula I':

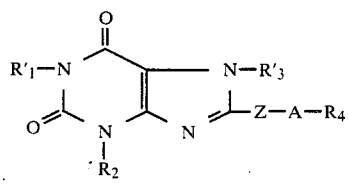

in which:

$R_2$, $R_4$, Z and A have the meanings previously defined;

$R'_1$ is selected from the group consisting of: alkyl radicals having from 1 to 5 carbon atoms inclusive in straight and branched chain, and $R'_3$ is selected from the group consisting of alkyl, hydroxyalkyl and dihydroxyalkyl radicals each containing from 1 to 5 carbon atoms inclusive; characterized in that:

a compound of the formula (II')

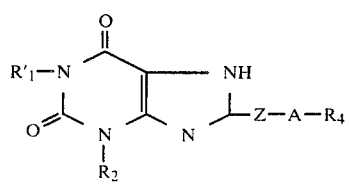

in which $R'_1$, $R_2$, $R_4$, Z and A have the above defined meanings is condensed with a halo compound of the formula III':

$$R'_3-X$$

in which $R'_3$ has the meaning previously defined and X is selected from the group consisting of a chlorine and a bromine atom.

The condensation is preferably carried out in a suitable solvent, such, for example, as dimethyl formamide, at a temperature between 80° and 120° C., in the presence of an acceptor of the hydracid formed during the reaction. This acceptor may be, among others, an alkaline carbonate, such, for example, as sodium and potassium carbonates.

The new compounds of the formula I may be converted by acids into salts of addition, which thus form part of the invention. As acids which may be used for the formation of these salts, there may for example be cited in the mineral series: hydrochloric, hydrobromic, sulphuric, phosphoric acids and in the organic series: acetic, propionic, maleic, fumaric, tartaric, citric, oxalic, benzoic, methane sulphonic and isethionic acids.

These new compounds may be purified by physical methods such as crystallisation, or chromatography, or chemical methods such as the formation of salts of addition with acids and decomposition of these salts by alkaline agents.

The compounds of the formula I and their physiologically tolerable salts possess useful pharmacological and therapeutic properties, in particular broncho-dilating, anti-allergic and phosphodiesterase inhibiting properties. Their toxicity is weak and their $LD_{50}$ determined on mice is greater than 100 mg/kg by intraperitoneal route and greater than 800 mg/kg by oral route.

The broncho-dilating activity has been studied in the guinea pig by the method of H. KONZETT and R. ROSSLER, Arch. Exp. U. Pharm. 195, 71 (1940). It has also been observed that the compounds of the present invention injected intravenously at doses varying according to the compounds from 1 to 5 mg/kg entirely inhibit the broncho-spasm caused by the intravenous administration either of histamine or serotonin and partially the effect of acetylcholine and of Slow Reacting Substance.

When submitted to the test of A. K. Armitage, Brit J. Pharmacol. 17, 196, (1961), the compounds according to the invention administered by oral route at doses between 0.5 and 10 mg/kg, depending on the compounds, inhibit by 50% the effect produced in the guinea pig by a histamine aerosol at 4%. For certain of these compounds, the effect is still very strong 48 hours after oral administration.

Morever, certain compounds according to the invention possess a specific agonist effect to the central and peripheral purinergic receptors of type A 1 and/or A 2 which can lead to a specificity of the therapeutic effect.

By way of non-restricting example, the oral administration of 5 mg/kg of the compound of example 1, inhibits for more than 48 hours the broncho-spasm caused be a histamine aerosol at 4%. In addition, a reduction of the anaphylactic cutaneous reaction is observed in the rat after a single administration of 20 mg/kg per os of this compound.

This compound of example 1 is more agonist to the A 2 receptors (IC 60=15 μM) than to the A 1 receptors (IC 50>100 μM).

The above described pharmacological properties as well as the weak toxicity of the compounds of the formula (I) and their physiologically tolerable salts enable them to be used in therapeutics in particular in the treatment of all the ailments where it is necessary to inhibit the antigenic—antibody reactions such as the auto-immune, allergic and inflammatory ailments and in particular those in which a broncho-dilating effect is welcome, such as asthmatic dyspnea and the chronic obstructive broncho-pneumophathies, in particular of spastic form. The long duration of action permits treatment of crisis as well as a basic treatment of simple or complex asthmatic ailments. In addition, the spasmolytic properties are indicated for the treatment of kidney and liver colics.

The present invention also has as its subject the pharmaceutical compositions containing as active principlea compound of the formula (I) or one of its physiologically tolerable salts, mixed or associated with an appropriate pharmaceutical excipient. These compositions are advantageously in unit dosage forms and may contain from 25 to 250 mg of active ingredient. The pharmaceutical compositions so obtained are advantageously presented in various forms, such, for example, as tablets, sugar-coated tablets, capsules, glossettes or galenic preparations appropriate for sub-lingual administration, suppositories, injectable or drinkable solutions as well as in the forms suitable for administration by aerosol.

They may be administered by oral, rectal or parenteral route at doses of 25 to 250 mg of active ingredient, once or twice a day.

The following examples, given in a nonrestrictive way, illustrate the invention. The melting points, unless otherwise stated have been determined by the Kofler heating plate.

EXAMPLE 1

1-methyl-3-isobutyl-8-[2-(4-diphenylmethyl-piperazinyl)ethyl]xanthine

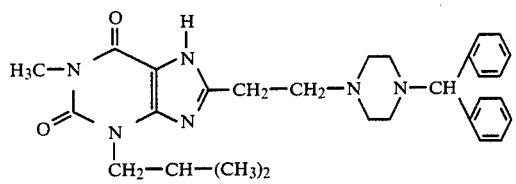

A suspension of 12.2 g of 1-methyl-3-isobutyl-8-bromoethylxanthine and of 23 g of benzyhydryl piperazine in 200 ml of ethanol is heated to reflux. Progressive dissolution is observed and heating is continued for 20-24 hours. After this the solution is evaporated to dryness and the residue is taken up by a 10% solution of sodium bicarbonate. This is extracted several times with $CH_2Cl_2$, dried on $Na_2SO_4$ and concentrated to dryness. The oily residue is purified by flash chromatography on 1 kg of silica 0.04-0.063 mm, eluting with ethyl acetate and then with a mixture of ethyl acetate and methanol (95/5). After fractionizing and evaporating the eluates, 14 g of pure product melting at 200°-202° C. is recovered.

The starting 1-methyl-3-isobutyl-8-bromoethylxanthine, melting at 210° C., has been prepared by bromiding with 48% HBr of the corresponding 8-methoxyethyl derivative, melting at 163° C., itself prepared by cyclization with NaOH of 1-isobutyl-b 3-methyl-2,4-dioxo-1,2,3,4-tetrahydro-5-(3-methoxypropionamido)-6-aminopyrimidine melting at 200° C., itself prepared by condensation of 3-methoxypropionic acid with 5,6-diamino-1-isobutyl-3-methyl-2,4-dioxo-1,2,3,4-tetrahydropyrimidine, itself prepared by reduction in the presence of Raney nickel as catalyst under a hydrogen pressure of 6 atmospheres, of the corresponding 5-nitroso derivative melting at 228° C., itself prepared by nitrosation with $NaNO_2/CH_3COOH$ of 1-isobutyl-3-methyl-2,4-dioxo-6-amino-1,2,3,4-tetrahydropyrimidine.

EXAMPLES 2-30

The following derivatives have been prepared according to the process described in example 1:

(2) 1,3-dimethyl-8-[(4-diphenylmethylpiperazinyl)methyl]-xanthine, M.P.: 241° C. (methanol).

(3) 1,3-dimethyl-8-[2-(4-diphenylmethylpiperazinyl)ethyl]-xanthine, M.P. (capillary): 103°-106° C. (methylene chloride).

(4) 1,3-dimethyl-8-[3-(4-diphenylmethylpiperazinyl)propyl]-xanthine, M.P. (capillary) of the corresponding dihydrochloride hemihydrate: 249°-250° C. (methanol).

(5) 1-methyl-3-isobutyl-8-[3-(4-diphenylmethylpiperazinyl)-propyl]xanthine, M.P. (capillary) of the corresponding dihydrochloride monohydrate: 217°-220° C. (ethanol).

(6) 1,3,7-trimethyl-8-[3-(4-diphenylmethylpiperazinyl)propyl]xanthine, M.P. of the corresponding fumarate: 198° C. (ethanol).

(7) 1,7-dimethyl-3-isobutyl-8-[3-(4-diphenylmethylpiperazinyl)propyl]xanthine, M.P. of the corresponding fumarate: 182° C. (ethanol/ether).

(8) 1,7-dimethyl-3-isobutyl-8-[2-(4-diphenylmethylpiperazinyl)ethyl]xanthine, M.P. (capillary) of the corresponding dihydrochloride: 214°-218° C. (n-propanol/ether).

(9) 1,7-dimethyl-3-phenyl-8-[3-(4-diphenylmethylpiperazinyl)propyl]xanthine, M.P.: 150° C. (isopropanol).

(10) 1-methyl-3-isobutyl-8-[2-(4-di[para-fluorophenyl]-methylpiperazinyl)ethyl]xanthine, M.P.: 184° C. (ethyl acetate).

(11) 1,7-dimethyl-3-isobutyl-8[2-(4-di[para-fluorophenyl]-methylpiperazinyl)ethyl]xanthine, M.P. of the corresponding dimaleate: 174° C. (n-propanol).

(12) 1,7-dimethyl-3-isobutyl-8-[3-(4-di[para-fluorophenyl]-methylpiperazinyl)propyl]xanthine, M.P. of the corresponding fumarate: 180° C. (ethanol).

(13) 1-methyl-3-isobutyl-8-[2-(N-[2-(N'-diphenylmethyl-N'-ethylamino)ethyl]-N-ethylamino)ethyl]xanthine, M.P. (capillary) of the corresponding dihydrochloride: 135°-140° C. (isopropanol/ether).

(14) 1,7-dimethyl-3-isobutyl-8-[2-(N-[2-(N'-diphenylmethyl-N'-ethylamino)ethyl]-N-ethylamino)ethyl]xanthine, M.P. (capillary) of the corresponding dihydrochloride: 130°-140° C. (isopropanol/ether).

(15) 1,7-dimethyl-3-isobutyl-8-[3-(N-[2-(N'-diphenylmethyl-N'-ethylamino)ethyl]-N-ethylamino)propyl]xanthine, M.P. (capillary) of the corresponding dihydrochloride: 125°-135° C.

(16) 1,7-dimethyl-3-n-propyl-8-[3-(4-diphenylmethylpiperazinyl)propyl]xanthine, M.P. of the corresponding fumarate: 200° C. (ethanol).

(17) 1-methyl-3-isobutyl-8-[2-(4-diphenylmethyloxypiperidino)ethyl]xanthine, M.P. (capillary) of the corresponding dihydrochloride: 163°-167° C. (isopropanol/ether).

(18) 1,7-dimethyl-3-isobutyl-8-[2-(4-diphenylmethyloxy-piperidino)ethyl]xanthine, M.P. (capillary) of the corresponding fumarate: 173°-177° C. (n-propanol).

(19) 1,7-dimethyl-3-isobutyl-8-[3-(4-diphenylmethyloxy-piperidino)propyl]xanthine, M.P. of the corresponding fumarate: 194° C. (ethanol).

(20) 1-methyl-3-isobutyl-8-[(4-diphenylmethyl-piperazinyl)-methyl]xanthine, M.P. 182° C.

(21) 1-methyl-3-isobutyl-8-[2-(4-di[para-fluorophenyl]-methylpiperazinyl)ethyl]xanthine, M.P. 200° C.

(22) 1-methyl-3-isobutyl-8-[2-(4-cinnamylpiperazinyl)ethyl]xanthine, M.P. 140° C. (methylene chloride).

(23) 1-ethyl-3-isobutyl-8-[3-(4-diphenylmethylpiperazinyl)-propyl]xanthine, M.P. (capillary) of the corresponding fumarate: 201°-205° C. (n-propanol).

(24) 1-ethyl-3-isobutyl-7-methyl-8-[3-(4-diphenylmethyl-piperazinyl)propyl]xanthine, M.P. of the corresponding maleate: 193° C. (n-propanol).

(25) 3-isobutyl-8-[2-(4-diphenylmethylpiperazinyl)ethyl]xanthine, M.P. 240° C. (ethyl acetate).

(26) 3-benzyl-8-[2-(4-diphenylmethylpiperazinyl)ethyl]xanthine, M.P. (capillary): 232°-235° C. (ethyl acetate).

(27) 1-methyl-3-isobutyl-7-(2,3-dihydroxypropyl)-8-[2-(4-diphenylmethylpiperazinyl)ethyl]xanthine, M.P. (capillary) of the corresponding dihydrochloride: 145°-150° C. (isopropanol/ether).

(28) 1-methyl-3-isobutyl-7-(2-hydroxyethyl)-8-[2-(4-diphenylmethylpiperazinyl)ethyl]xanthine, M.P. (capillary) of the corresponding dihydrochloride: 190°-200° C. (isopropanol/ether).

(29) 1-R,S methyl-3-isobutyl-8-[1-hydroxy-2-(4-diphenylmethyl)ethyl]xanthine, M.P. 212° C. (ether).

(30) 3-isobutyl-8-[1-hydroxy-2-(4-diphenylmethylpiperazinyl)ethyl]xanthine, M.P. 234° C., with decomposition (ethyl acetate).

The products which are the subjects of examples 2-30 have been prepared starting from compounds of the formula (II$_a$, the characteristics of which are summarized below in Table A. These products of the formula (II$_a$) have themselves been prepared according to the process which is the subject of the operational scheme previously given, starting from compounds, the characteristics of which are summarized below in Tables B, C and D.

TABLE (A)

Compounds of the formula (II$_a$):

| R$_1$ | R$_2$ | R$_3$ | Z | M.P. (Kofler) in °C. |
|---|---|---|---|---|
| CH$_3$ | CH$_3$ | H | (CH$_2$)$_2$ | 227 |
| CH$_3$ | CH$_3$ | H | (CH$_2$)$_3$ | 220 |
| CH$_3$ | CH$_3$ | CH$_3$ | (CH$_2$)$_3$ | 130 |
| CH$_3$ | —CH$_2$—CH—(CH$_3$)$_2$ | H | —CH$_2$ | 224 |
| CH$_3$ | —CH$_2$—CH—(CH$_3$)$_2$ | H | (CH$_2$)$_2$ | 210 |
| CH$_3$ | —CH$_2$—CH—(CH$_3$)$_2$ | H | (CH$_2$)$_3$ | 182 |
| CH$_3$ | —CH$_2$—CH—(CH$_3$)$_2$ | CH$_3$ | (CH$_2$)$_2$ | 114 |
| CH$_3$ | —CH$_2$—CH—(CH$_3$)$_2$ | CH$_3$ | (CH$_2$)$_3$ | 100 |

TABLE (A)-continued

Compounds of the formula (II$_a$):

| R$_1$ | R$_2$ | R$_3$ | Z | M.P. (Kofler) in °C. |
|---|---|---|---|---|
| CH$_3$ | —CH$_2$—CH$_2$—CH$_3$ | CH$_3$ | (CH$_2$)$_3$ | 92 |
| CH$_3$ | —CH$_2$—CH—(CH$_3$)$_2$ | H | (CH$_2$)$_3$ | 166 |
| CH$_3$ | —CH$_2$—C$_6$H$_5$ (benzyl) | CH$_3$ | (CH$_2$)$_3$ | 156 |
| C$_2$H$_5$ | —CH$_2$—CH—(CH$_3$)$_2$ | H | (CH$_2$)$_3$ | 172 |
| H | —CH$_2$—C$_6$H$_5$ (benzyl) | H | (CH$_2$)$_2$ | 252 |
| H | —CH$_2$—CH—(CH$_3$)$_2$ | H | (CH$_2$)$_2$ | 292–294 |
| *CH$_3$ | —CH$_2$—CH—(CH$_3$)$_2$ | H | —CH—CH$_2$<br>  \|<br>  OH | 160 |
| *H | —CH$_2$—CH—(CH$_3$)$_2$ | H | —CH—CH$_2$<br>  \|<br>  OH | 250 |

The compounds * were prepared by analogy with G. EHRHART and als, Arch. der Pharm. 289, 453–59 (1956), according to the following scheme:

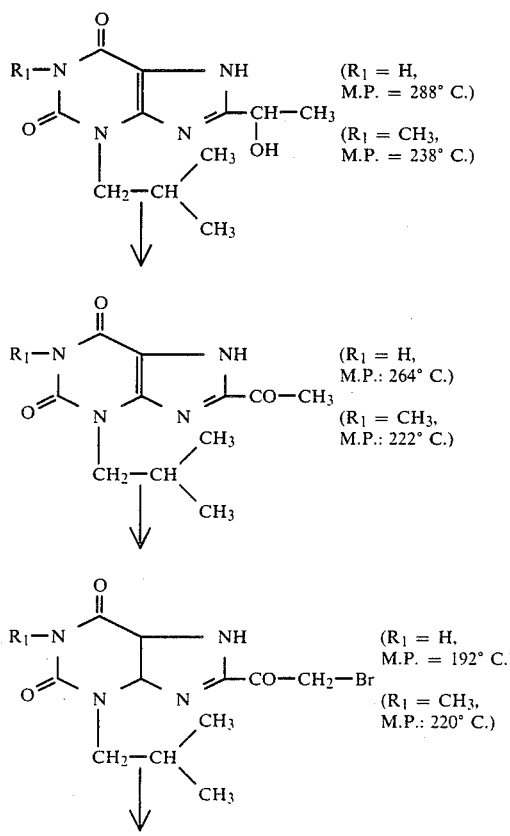

-continued

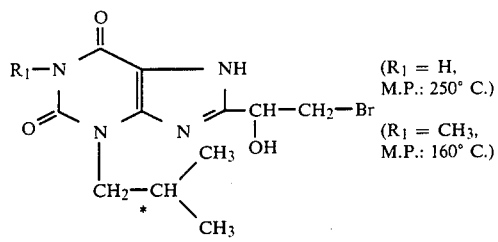

(R₁ = H, M.P.: 250° C.)
(R₁ = CH₃, M.P.: 160° C.)

TABLE (B)

Compounds of the formula:

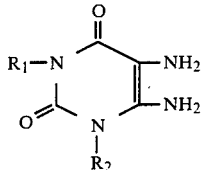
(VI)

| R₁ | R₂ | M.P. (Kofler) in °C. |
|---|---|---|
| CH₃ | CH₃ | 210–214 |
| CH₃ | —CH₂—CH—(CH₃)₂ | 174 |
| CH₃ | —CH₂—CH=CH₂ | 116 |
| CH₃ | —CH₂—CH—(CH₃)₂ | 172 |
| CH₃ | —⟨phenyl⟩ | 250–252 |
| C₂H₅ | —CH₂—CH—(CH₃)₂ | amorphe |
| H | —CH₂—⟨phenyl⟩ | 243–244 |
| H | —CH₂—CH—(CH₃)₂ | not isolated |

TABLE (C)

Compounds of the formula:

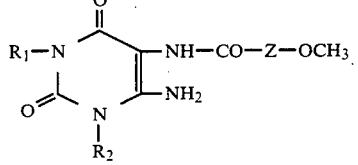
(VII)

| R₁ | R₂ | Z | M.P. (Kofler) in °C. |
|---|---|---|---|
| CH₃ | CH₃ | (CH₂)₂ | 208 |
| CH₃ | CH₃ | (CH₂)₃ | 221 |
| CH₃ | —CH₂—CH—(CH₃)₂ | CH₂ | amorphous |
| CH₃ | —CH₂—CH—(CH₃)₂ | (CH₂)₂ | 200 |
| CH₃ | —CH₂—CH—(CH₃)₂ | (CH₂)₃ | 150 |
| CH₃ | —CH₂—CH=CH₂ | (CH₂)₃ | amorphous |
| C₂H₅ | CH₂—CH—(CH₃)₂ | (CH₂)₃ | amorphous |
| CH₃ | —⟨phenyl⟩ | (CH₂)₃ | amorphous |
| H | —CH₂—⟨phenyl⟩ | (CH₂)₂ | 190 |
| H | —CH₂—CH—(CH₃)₂ | (CH₂)₂ | 158 |

TABLE (D)

Compounds of the formula:
Derive de formule:

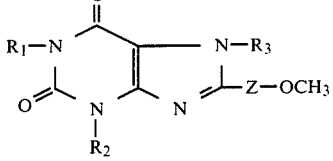
(IX)

| R₁ | R₂ | R₃ | Z | M.P. (Kofler) in °C. |
|---|---|---|---|---|
| CH₃ | CH₃ | H | (CH₂)₂ | 198 |
| CH₃ | CH₃ | H | (CH₂)₃ | 192 |
| CH₃ | CH₃ | CH₃ | (CH₂)₂ | 156 |
| CH₃ | CH₃ | CH₃ | (CH₂)₃ | 96 |
| CH₃ | —CH₂—CH—(CH₃)₂ | H | CH₂ | 196 |
| CH₃ | —CH₂—CH—(CH₃)₂ | H | (CH₂)₂ | 165 |
| CH₃ | —CH₂—CH—(CH₃)₂ | H | (CH₂)₃ | 144 |
| CH₃ | —CH₂—CH—(CH₃)₂ | CH₃ | (CH₂)₂ | 82 |
| CH₃ | —CH₂—CH—(CH₃)₂ | CH₃ | (CH₂)₃ | 76 |
| CH₃ | —CH₂—CH=CH₂ | H | (CH₂)₃ | 160 |
| CH₃ | —CH₂—CH=CH₂ | CH₃ | (CH₂)₃ | 44–45 |
| CH₃ | —CH₂—CH₂—CH₃* | CH₃ | (CH₂)₃ | 67 |
| C₂H₅ | —CH₂—CH—(CH₃)₂ | H | (CH₂)₃ | 137–139 |
| C₂H₅ | —CH₂—CH—(CH₃)₂ | CH₃ | (CH₂)₃ | 80 |
| CH₃ | —⟨phenyl⟩ | H | (CH₂)₃ | 216 |
| CH₃ | —⟨phenyl⟩ | CH₃ | (CH₂)₃ | 163 |
| H | —CH₂—⟨phenyl⟩ | H | (CH₂)₂ | 190 |
| H | —CH₂—CH—(CH₃)₂ | H | (CH₂)₂ | 250 |

*This 3-propyl compound was prepared by reducing the corresponding 3-allyl compound, under a hydrogen pressure of 606.10³ Pa in the presence of nickel as catalyst.

N.B.: The compounds of formula VI were prepared according to the following scheme:

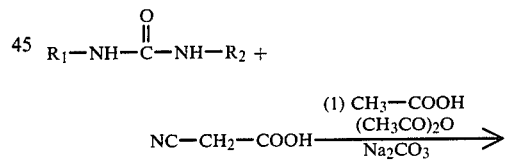

$$NC-CH_2-COOH \xrightarrow[Na_2CO_3]{(1) CH_3-COOH \atop (CH_3CO)_2O}$$

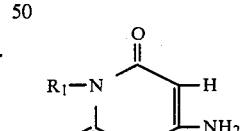

by analogy with the method of
John H. SPEER and Albert L. RAYMOND,
J.A.C.S. (1953) 75, 114

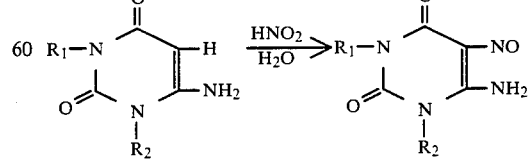

by analogy with the method of G. N. KRUTOV-SKIKH and als, Pharmaceutical Chemistry Journal (1977) 11(2), 224

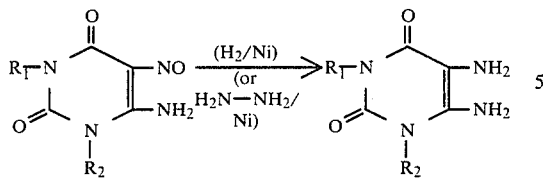

EXAMPLE 31

1-methyl-3-isobutyl-7-(2-hydroxyethyl)-8-[2-(4-diphenylmethylpiperazinyl)ethyl]xanthine

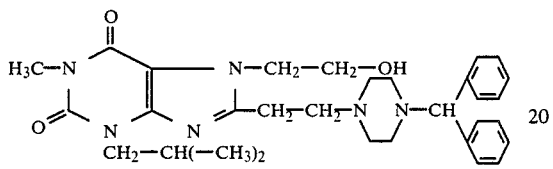

10 g of 1-methyl-3-isobutyl-8[2-(4-diphenylmethylpiperazinyl)ethyl]xanthine and 37.6 g of potassium carbonate were stirred in 200 ml of dimethyl formamide, then heated up to 100° C. 10 ml of glycol chlorohydrin were quickly added and the mixture was stirred at 110° C. for one hour. Then 20 ml of glycol chlorohydrin were quickly added and the mixture was stirred at 110° C. for one hour. Next 40 g of potassium carbonate, and after which 20 ml of glycol chlorohydrin were added. The mixture was maintained at 110° C. for 3 and a half hours then at room temperature for 72 hours. The mixture was then concentrated to dryness. The residue was taken off with a mixture of methylene chloride and water. The organic phase was dried on sodium sulfate then concentrated to dryness. A chromatography was carried out on 750 g of silica (0.04–0.063 mm). The elution was performed first with pure ethyl acetate next with a mixture ethyl acetate-methanol (95–5) and finally with a mixture ethyl acetate-methanol (90–10).

8.6 g of base were obtained and dissolved in 50 ml of isopropanol. Ether hydrochloric was added until the medium becomes slightly acid. The hydrochlorate of the waited product was precipitated out with a large excess of anhydrous ether. It was suctioned off and washed with ether. After drying at 115° C. under a pressure of 0.6 mmHg, 8.7 g of 1-methyl-3-isobutyl-7-(2-hydroxyethyl)-8-[2-(4-diphenylmethylpiperazinyl)ethyl]xanthine dihydrochloride were obtained; M.P. (capillary) 190°–200° C. (isopropanol/ether); yield: 71%.

EXAMPLE 32

The following compound was prepared according to the same method:

1-methyl-3-isobutyl-7-(2,3-dihydroxypropyl)-8-[2-(4-diphenylmethylpiperazinyl)ethyl]xanthine, M.P. (capillary) of the corresponding dihydrochloride: 145°–155° C. (isopropanol/ether).

We claim:

1. A compound selected from the group consisting of: xanthine compounds of the formula I:

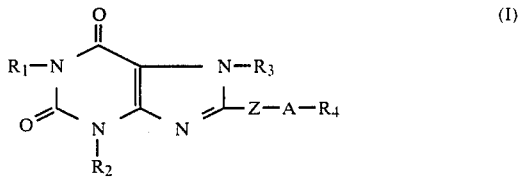

in which:

$R_1$ is selected from the group consisting of: hydrogen, and straight and branched alkyl having from 1 to 5 carbon atoms inclusive;

$R_2$ is selected from the group consisting of straight and branched hydrocarbon radicals having up to 6 carbon atoms inclusive, and these radicals having a double bond, phenyl, and benzyl;

$R_3$ is selected from the group consisting of hydrogen and alkyl, hydroxy alkyl and dihydroxyalkyl each having from 1 to 5 carbon atoms inclusive;

$R_4$ is selected from the group consisting of the group of the formula;

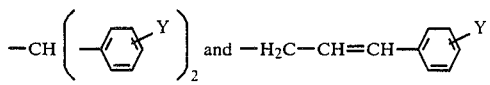

in which

Y is selected from the group consisting of hydrogen, halogen, alkyl and alkoxy each having from 1 to 5 carbon atoms inclusive, and hydroxyl;

Z is selected from the group consisting of methylene and hydrocarbon radicals having from 2 to 5 carbon atoms and these hydrocarbon radicals substituted by hydroxyl, and A is selected from the group consisting of the amino residues of the formula:

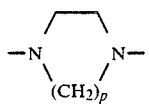

in which p is selected from the integers 2 and 3,

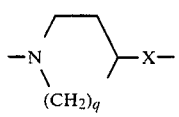

in which q is selected from the integers 1 and 2, and

X is selected from the group consisting of a double bond oxygen and

in which $R_5$ is selected from the group consisting of hydrogen and alkyl and alkoxy each having from 1 to 5 carbon atoms inclusive; and

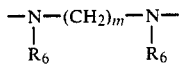

in which
m is selected from the integers from 2 to 6; and
R₆ is selected from the group consisting of alkyls having from 1 to 5 carbon atoms inclusive; and
physiologically tolerable acid addition salts thereof.

2. A compound of claim 1 which is 1-methyl-3-isobutyl-8[2-(4-diphenylmethylpiperazinyl)ethyl]xanthine.

3. A compound of claim 1 which is 1-methyl-3-isobutyl-8-[3-(4-diphenylmethylpiperazinyl)propyl]xanthine.

4. A compound of claim 1 which is 1,7-dimethyl-3-isobutyl-8-[3-(4-diphenylmethylpiperazinyl)propyl]xanthine.

5. A compound of claim 1 which is 1-methyl-3-isobutyl-8-[2-(4-diphenylmethylpiperazinyl)ethyl]xanthine.

6. A compound of claim 1 which is 1,7-dimethyl-3-isobutyl-8-[3-(4-di[parafluorophenyl]methylpiperazinyl)propyl]xanthine.

7. A compound of claim 1 which is 1-methyl-3-isobutyl-8-[2-(4-diphenylmethylpiperidine)ethyl]xanthine.

8. A compound of claim 1 which is 1,7-dimethyl-3-isobutyl-8-[3-(4-diphenylmethylpiperidino)propyl]xanthine.

9. A compound of claim 1 which is 1-methyl-3-isobutyl-8-[2-(4-di[para-fluorophenyl]methylpiperazinyl)ethyl]xanthine.

10. A compound of claim 1 which is 3-isobutyl-8-[2-(4-diphenylmethylpiperazinyl)ethyl]xanthine.

11. A compound of claim 1 which is 1-methyl-3-isobutyl-7-(2,3-dihydroxypropyl)-8-[2-(4-diphenylmethylpiperazinyl)ethyl]xanthine.

12. A pharmaceutical composition suitable for use for its broncho-dilating, anti-allergic and phosphodiesterase inhibiting properties, containing as active ingredient a compound of claim 1, together with a suitable pharmaceutical carrier.

13. A method for treating a living animal body afflicted with a disease where it is necessary to inhibit the antigenic-antibody reactions comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,548,820

DATED : October 22, 1985

INVENTOR(S) : Gilbert Regnier, Claude Guillonneau, Jacques Duhault and Michelle Boulanger It is certified that error appears in the above-identified patent and that said Letters Patent is hereby corrected as shown below:

Title page, [56] References Cited, FOREIGN PATENT DOCUMENTS;
  "0095188" should read -- 56-95188 --
Col. 4, line 58; "Morever" should read -- Moreover --
Col. 4, line 64; "be" should read -- by --
Col. 5, line 20; "principlea" should read -- principle a --
Col. 5, line 54; "benzyhydryl" should read -- benzhydryl --
Col. 6, line 3; "-isobutyl-b 3-methyl-" should read -- -isobutyl-3-methyl- --
Col. 9, approximately line 33; "amorphe" should read -- amorphous --

Signed and Sealed this

Eleventh Day of February 1986

[SEAL]

Attest:

DONALD J. QUIGG

Attesting Officer

Commissioner of Patents and Trademarks